(12) United States Patent
Pettit et al.

(10) Patent No.: US 8,415,294 B2
(45) Date of Patent: Apr. 9, 2013

(54) CYCLODEPSIPEPTIDES WITH ANTINEOPLASTIC ACTIVITY AND METHODS OF USING TO INHIBIT CANCER AND MICROBIAL GROWTH

(75) Inventors: George R. Pettit, Paradise Valley, AZ (US); Rui Tan, Mesa, AZ (US); Robin K. Pettit, Fort McDowell, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 0 days.

(21) Appl. No.: 12/598,943

(22) PCT Filed: Jun. 5, 2008

(86) PCT No.: PCT/US2008/065976
§ 371 (c)(1),
(2), (4) Date: Apr. 7, 2010

(87) PCT Pub. No.: WO2009/011988
PCT Pub. Date: Jan. 22, 2009

(65) Prior Publication Data
US 2010/0197570 A1   Aug. 5, 2010

Related U.S. Application Data

(60) Provisional application No. 60/942,058, filed on Jun. 5, 2007.

(51) Int. Cl.
*A61K 38/15* (2006.01)
*A61K 38/04* (2006.01)
*A61K 38/12* (2006.01)
*C07K 7/50* (2006.01)

(52) U.S. Cl.
USPC .............. 514/2.6; 514/2.7; 514/2.8; 514/2.9; 530/323

(58) Field of Classification Search .................. None
See application file for complete search history.

(56) References Cited

U.S. PATENT DOCUMENTS

| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,059,595 A | 10/1991 | Le Grazie |
| 5,073,543 A | 12/1991 | Marshall et al. |
| 5,120,543 A | 6/1992 | Hagin et al. |
| 5,354,556 A | 10/1994 | Sparks et al. |
| 5,591,767 A | 1/1997 | Mohr et al. |
| 5,639,476 A | 6/1997 | Oshlack et al. |
| 5,674,533 A | 10/1997 | Santus et al. |

(Continued)

OTHER PUBLICATIONS

Risperantin, a novel insecticidal cyclodepsipeptides from Streptomyces. Journal of Antibiotics (1993). 46(4) 701-703.*

(Continued)

*Primary Examiner* — Robert A Wax
*Assistant Examiner* — Danah Al-Awadi
(74) *Attorney, Agent, or Firm* — Quarles & Brady LLP

(57) ABSTRACT

The present invention is directed to cyclodepsipeptide compounds having antineoplastic and/or antimicrobial activity, preferably Kitastatin 1. The present invention is further directed to methods of inhibiting cancer cell growth and/or microbial growth in a host inflicted therewith by administering cyclodepsipeptide compounds to the inflicted host.

18 Claims, 1 Drawing Sheet

1, $R_1$ = $CH_2CH(CH_3)_2$, $R_2$ = CHO, respirantin

2, $R_1$ = $CH(CH_3)_2$, $R_2$ = CHO

3, $R_1$ = $CH_2CH(CH_3)_2$, $R_2$ = H, kitastatin 1

U.S. PATENT DOCUMENTS

| | | | |
|---|---|---|---|
| 5,733,566 A | | 3/1998 | Lewis |
| 6,034,058 A | * | 3/2000 | Rinehart et al. ............ 514/19.3 |
| 6,680,311 B1 | | 1/2004 | Al-Awar et al. |

OTHER PUBLICATIONS

Dermer (Bio?technolgoy, 1994,12:320.*
Chung et al., Int. J. Syst. Bacteriol., 49:753-758 (1999).
Wanigasekera et al., Biosci. Biotechnol. Biochem., 65:2353-2357 (2001).
Baker et al., J. Tetrahedron Lett., 28:5565-5568 (1987).
Caruso et al., Annals of Microbiology, 50:89-102 (2000).
Kretschmer et al., Agric. Biol. Chem., 49:2509-2511 (1985).
Meyer et al., Helv. Chim. Acta, 68:83-94 (1985).
Momose et al., J. Antibiot. (Tokyo), 54:1004-1012 (2001).
Moon et al., J. Antibiot. (Tokyo), 56:856-861 (2003).
Mordarska et al., Arch. Immunol. Ther. Exp. (Warsz.), 35:237-247 (1987).
NCCLS. Methods for Dilution Antimicrobial Susceptibility Tests for Bacteria That Grow Aerobically; Approved. Standard—Fifth Edition. NCCLS document M7-A5 [ISBN 1-56238-394-9]. NCCLS, 940 West Valley Road, Suite 1400, Wayne, Pennsylvania 19087-1898 USA, 2000.
NCCLS. Reference Method for Broth Dilution Antifungal Susceptibility Testing of Yeasts; Approved Standard—Second Edition. NCCLS document M27-A2 [ISBN 1-56238-469-4]. NCCLS, 940 West Valley Road, Suite 1400, Wayne, Pennsylvania 19087-1898 USA, 2002. NCCLS. Reference Method for Broth Dilution Antifungal Susceptibility Testing of Yeasts; Approved Standard—Second Edition. NCCLS Document M27-A2; 2002.
O'Shea et al., J. Antibiot. (Tokyo), 50:1073-1077 (1997).
Peczynska-Czoch et al., Arch. Immunol. Ther. Exp. (Warsz.), 35:109-115 (1987).
Peczynska-Czoch, Arch. Immunol. Ther. Exp. (Warsz.), 35:129-137 (1987).
Pettit et al., J. Nat. Prod., 68:1450-1458, 1191-1197, 207-211, 729-733, 1253-1255, 974-978, 1256-1258, 60-63 (2005).
Scheidt et al., J. Am. Chem. Soc., 124:6981-6990 (2002).
Smith et al., Org. Lett., 7:4403-4406 (2005).
Suzuki et al., Jpn. Kokai Tokkyo Koho, 15 pp. CODEN: JKXXAF JP 06239844 A2 19940830 Heisei. Application: JP 93-51415 19930217 (1994).
Tamamura et al., J. Antibiot. (Tokyo), 38:1664-1669 (1985).
Toshima et al., Tetrahedron Lett., 37:1073-1076 (1996).
Urushibata et al., J. Antibiot. (Tokyo), 46:701-703 (1993).
Werner et al., J. Antibiot. (Tokyo), 37:110-117 (1984).
Werner et al., Tetrahedron Lett., 24:5193-5196 (1983).

* cited by examiner

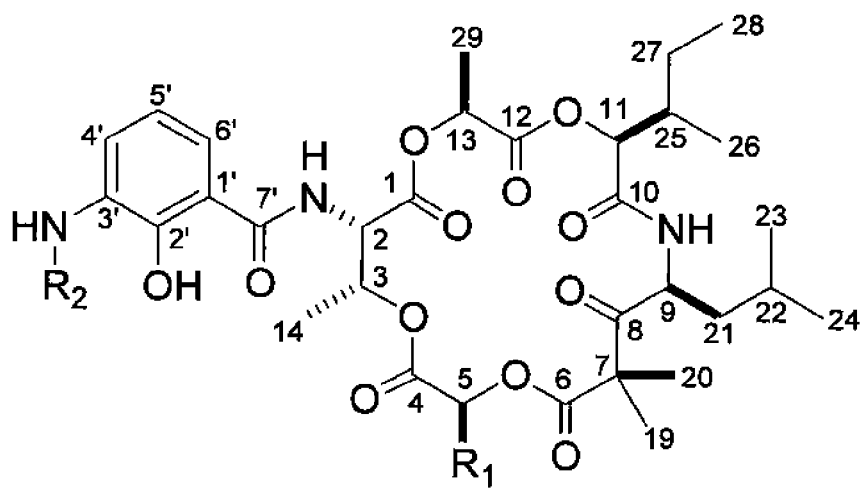
1, R₁ = CH₂CH (CH₃)₂, R₂ = CHO, respirantin
2, R₁ = CH (CH₃)₂, R₂ = CHO
3, R₁ = CH₂CH (CH₃)₂, R₂ = H, kitastatin 1

CYCLODEPSIPEPTIDES WITH ANTINEOPLASTIC ACTIVITY AND METHODS OF USING TO INHIBIT CANCER AND MICROBIAL GROWTH

CROSS-REFERENCE TO RELATED PATENT APPLICATIONS

The present application is filed pursuant to 35 U.S.C. 371 as a U.S. National Phase application of International Patent Application No. PCT/US08/65976, which was filed Jun. 5, 2008, claiming the benefit of priority to U.S. Patent Application No. 60/942,058, which was filed on Jun. 5, 2007. The entire text of the aforementioned applications is incorporated herein by reference in its entirety.

STATEMENT OF FEDERALLY SPONSORED RESEARCH

Financial assistance for this invention was provided by the United States Government, through the Division of Cancer Treatment and Diagnosis, National Cancer Institute, DHHS by Outstanding Investigator Grant CA44344-03-12 and RO1 CA90441-01-05. Therefore, the United States Government may own certain rights to this invention.

FIELD OF THE INVENTION

The present invention is directed to cyclodepsipeptide compounds having antineoplastic and/or antimicrobial activity. The present invention is further directed to methods of inhibiting cancer cell growth and/or microbial growth in a host inflicted therewith by administering cyclodepsipeptide compounds to the inflicted host.

BACKGROUND OF THE INVENTION

The actinomycete genus *Kitasatospora* has a developing history of producing biologically active metabolites, especially those with cancer cell growth inhibitory properties. An early example of the latter was the isolation of the anticancer antibiotic terpentecin from a soil *Kitasatospora* sp. (strain MF730-N6) by Umezawa and colleagues in 1985.[2] That advance was quickly followed by the isolation of anticancer carbolines from *Kitasatospora setae*[3a,b] cultured from a Spitsbergen soil sample.[4] In 1993, the stereochemically undefined cyclodepsipeptide respirantin (1) was isolated from a *Kitasatospora* sp. during an examination of its constituents for insecticidal activity.[5] Interestingly, in an investigation of endophytic actinomycetes on *Taxus baccata* plants, a *Kitasatospora* sp. (strain P & U 22869) was isolated and found to produce taxol and related taxanes.[6] More recently, *Kitasatospora* spp. have been found to produce yeast-like pleiotropic drug-resistant pump constituents,[7] proteasome inhibitors designated tyropeptins A and B,[8] and bafilomycin-like antifungal compounds[9]; more recently, *K. cheerisanensis* was found to contain the cytotoxic bafilomycin C1-amide.[10] The bafilomycins represent a group of 16-membered macrocyclic lactones isolated from *K. setae* and several streptomyces species and are very strong cancer-cell-growth inhibitors.[11a-h]

SUMMARY OF THE INVENTION

The present invention is directed to novel cyclodepsipeptide compounds. Preferably, the compound is in a substantially pure form having the structural formula

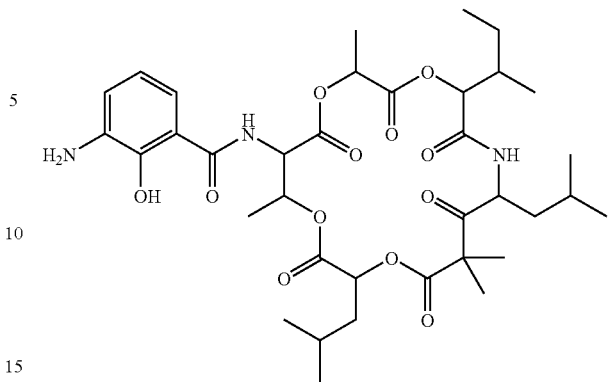

and more preferably, the compound is denominated as Kitastatin 1 having the structural formula:

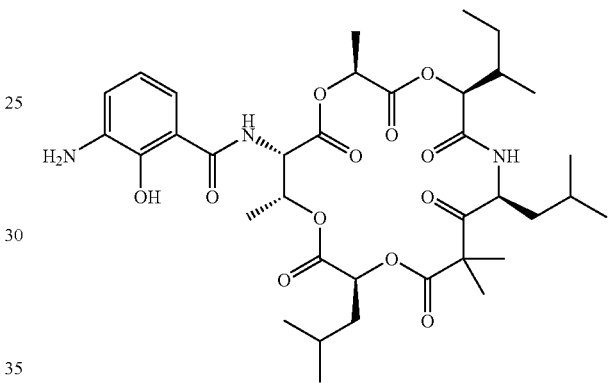

In one embodiment the compound is in a pharmaceutically acceptable carrier. Preferably, the compound is in a therapeutically effective amount sufficient to inhibit cancer cell growth or to inhibit the growth of a parasitic microbe.

The present invention is further directed methods of inhibiting cancer cell growth in a host inflicted therewith by administering a cyclodepsipeptide compound to the inflicted host. Preferably, the host is a human and the method comprises administering to the host a therapeutically effective amount of a compound having the structural formula:

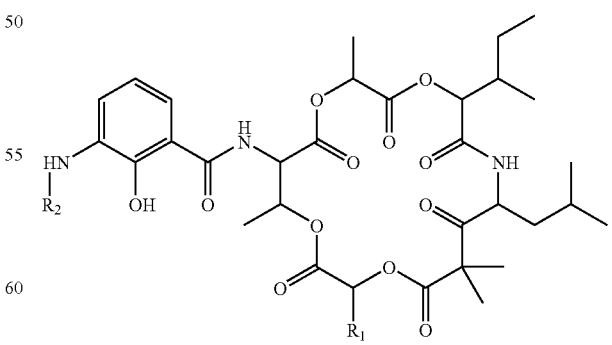

or salts thereof, wherein
$R_1$ is $CH_2CH(CH_3)_2$ or $CH(CH_3)_2$; and
$R_2$ is CHO or H.

In one nonlimiting embodiment, $R_1$ is $CH_2CH(CH_3)_2$ and $R_2$ is H. More preferably, the compound has the structural formula:

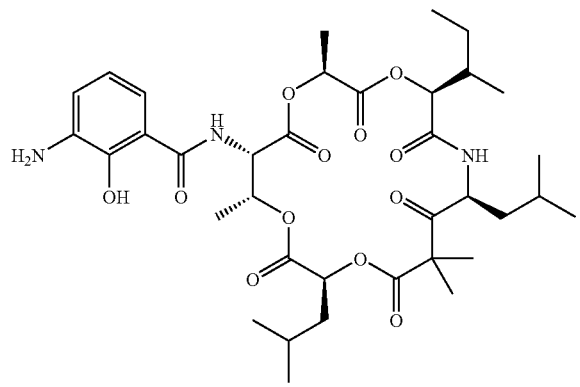 [SMILES: CCC(C)[C@@H]1OC(=O)[C@H](C)OC(=O)[C@@H](NC(=O)c2cccc(N)c2O)[C@@H](C)OC(=O)[C@H](CC(C)C)OC(=O)C(C)(C)C(=O)[C@H](CC(C)C)NC1=O]

The compounds can be administered alone or more preferably the compound is administered in a pharmaceutically acceptable carrier.

In a preferred embodiment, the method is used to inhibit the growth of one or more cancer cells selected from the group consisting of: leukemia, pancreas, breast, CNS, lung-NSC, colon, or prostate cancer.

The compounds of the present invention can advantageously be used to inhibit microbial growth. In one embodiment, the invention is directed to a method of inhibiting microbial growth. The method preferably comprises contacting a microbe with a therapeutically effective amount of a compound of the invention. The compound used can be one or more cyclodepsipeptide compounds or salts thereof in an amount sufficient to inhibit the microbial growth. Preferably the compound used to inhibit microbial growth has the structural formula:

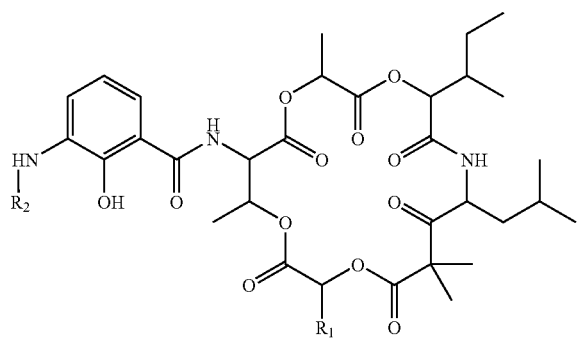

wherein
$R_1$ is $CH_2CH(CH_3)_2$ or $CH(CH_3)_2$; and
$R_2$ is CHO or H.

One preferred compound having anti-microbial growth activity has the following structural formula:

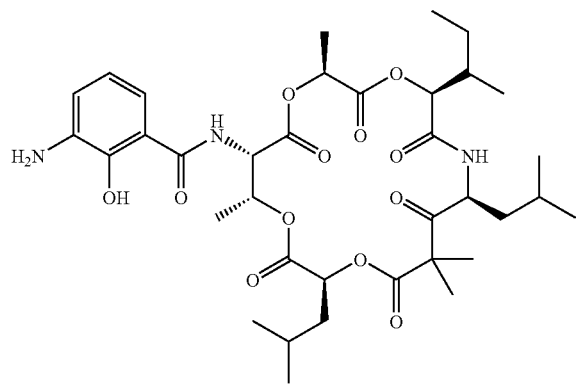 [SMILES: CCC(C)[C@@H]1OC(=O)[C@H](C)OC(=O)[C@@H](NC(=O)c2cccc(N)c2O)[C@@H](C)OC(=O)[C@H](CC(C)C)OC(=O)C(C)(C)C(=O)[C@H](CC(C)C)NC1=O]

In one embodiment, the step of contacting the microbe with the compound is accomplished by administering the compound to a host infected with the microbe. Advantageously, the host is preferably a human and the compound used inhibits the growth of at least one of the following microbes: *Cryptococcus neoformans*, *Enerococus faecalis*, *Micrococcus luteus*, *Stenotrophomonas maltophilia*, *Micrococcus luteus*, *Staphylococcus aureus*, *Escherichia coli*, *Enterobacter cloacae*, *Steptococcus pneumoniae*, *Neisseria gonorrhoeae*, or *Candida albicans*; and, more preferably, at least *Cryptococcus neoformans*, *Enerococus faecalis*, or *Micrococcus luteus*.

BRIEF DESCRIPTION OF THE DRAWINGS

FIG. 1 shows cyclodepsipeptides 1-3, wherein cyclodepsipeptide 1 is respirantin, cyclodepsipeptide 2 is a valeryl homologue, and cyclodepsipeptide 3 is kitastatin 1.

DETAILED DESCRIPTION OF THE INVENTION

As described above, the present invention is directed to novel cyclodepsipeptide compounds. Reference to a compound of the invention herein is understood to include reference to salts thereof, unless otherwise indicated. The term "salt(s)", as employed herein, denotes acidic and/or basic salts formed with inorganic and/or organic acids and bases. Salts of the compounds of the invention may be formed, for example, by reacting the compound with an amount of acid or base, such as an equivalent amount, in a medium such as one in which the salt precipitates or in an aqueous medium followed by lyophilization. Formation of salts is well within the ability of one skilled in the art. Examples of specific salts of the compound of the invention are provided herein, but are not intended to be limiting.

Preferred compounds of the invention inhibit the growth of cancer cells and/or parasitic microbial growth. Preferably, the compound inhibits cancer cells, and more preferably the compounds inhibit one or more cancer cells selected from the group consisting of leukemia, pancreas, breast, CNS, lung-NSC, colon, or prostate cancer.

In another embodiment, a method is provided for inhibiting the growth of cancer cells in a host. The method comprises administering to a host inflicted with cancer at least one cyclodepsipeptide compound disclosed herein. Preferably, the compound is administered in a pharmaceutical composition. Preferred pharmaceutical compositions are discussed in detail below. The compound administered is typically in a therapeutically effective amount sufficient to inhibit the cancer cell growth in the host. The host is preferably an animal, more preferably a mammal, and most preferably a human.

In certain embodiments, the method comprises administering to a host in need thereof an effective amount of a compound of the invention and at least one additional therapeutic agent. In one embodiment, the additional therapeutic agent is a chemotherapeutic agent including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, docetaxel, and mixtures thereof.

In another embodiment, the invention is directed to a method of inhibiting microbial growth, preferably in a host as described above. The method comprises administering to a host at least one cyclodepsipeptide compound disclosed herein in a therapeutically effective amount sufficient to inhibit the microbial growth in the host. The compounds of invention can be administered, alone or in combination with one or more additional antimicrobial agents, to treat microbial infections such as fungal infections and bacterial infections, or combinations of such infections.

Accordingly, in one specific embodiment the invention is a method for treating a microbial infection wherein the fungal infection is resistant to, or sensitive to, an azole antifungal agent, such as fluconazole. The methods of the invention may further include co-administration of a second antimicrobial agent, resulting in administration of an additional antifungal agent and/or an antibacterial agent.

Fungal infections include fungal infections (mycoses), which may be cutaneous, subcutaneous, or systemic. Superficial mycoses include tinea capitis, tinea corporis, tinea pedis, onychomycosis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections include opportunistic fungal infections, particularly in immunocompromised patients such as those with AIDS. Fungal infections contribute to meningitis and pulmonary or respiratory tract diseases.

Pathogenic organisms include dermatophytes (e.g., *Microsporum canis* and other *M.* spp.; and *Trichophyton* spp. such as *T. rubrum*, and *T. mentagrophytes*), yeasts (e.g., *Candida albicans, C. Tropicalis*, or other *Candida* species), *Torulopsis glabrata, Epidermophyton floccosum, Malassezia fuurfur* (*Pityropsporon orbiculare*, or *P. ovale*), *Cryptococcus neoformans, Aspergillus fumigatus*, and other *Aspergillus* spp., *Zygomycetes* (e.g., *Rhizopus, Mucor*), *Paracoccidioides brasiliensis, Blastomyces dermatitides, Histoplasma capsulatum, Coccidioides immitis*, and *Sporothrix schenckii*. Fungal infections include *Cladosporium cucumerinum, Epidermophyton floccosum*, and *Microspermum ypseum*. Examples of current antimycotic drugs include nystatin, clotrimazole, amphotericin B, ketoconazole, fluconazole, and itraconazole.

Bacterial infections result in diseases such as bacteremia, pneumonia, meningitis, osteomyelitis, endocarditis, sinusitis, arthritis, urinary tract infections, tetanus, gangrene, colitis, acute gastroenteritis, bronchitis, and a variety of abscesses, nosocomial infections, and opportunistic infections. Bacterial pathogens include Gram-positive cocci such as *Staphylococcus aureus, Streptococcus pyogenes* (group A), *Streptococcus* spp. (viridans group), *Streptococcus agalactiae* (group B), *S. bovis, Streptococcus* (anaerobic species), *Streptococcus pneumoniae*, and *Enterococcus* spp.; Gram-negative cocci such as *Neisseria gonorrhoeae, Neisseria meningitidis*, and *Branhamella catarrhalis*; Gram-positive bacilli such as *Bacillus anthracis, Corynebacterium diphtheriae* and *Corynebacterium* species which are diptheroids (aerobic and anerobic), *Listeria monocytogenes, Clostridium tetani, Clostridium difficile, Escherichia coli, Enterobacter species, Proteus mirablis* and other spp., *Pseudomonas aeruginosa, Klebsiella pneumoniae, Salmonella, Shigella, Serratia*, and *Campylobacter jejuni*.

Preferably, the compound used inhibits a microbe from the genus *Neisseria, Enterococcus, Streptococcus* or *Cryptococcus* and even more preferably the compound inhibits a microbe selected from the group consisting of: *Neisseria gonorrhoeae; Enterococcus faecalis; Streptococcus pneumoniae*; and *Cryptococcus neoformans*.

Pharmaceutical Compositions and Dosage Forms

Pharmaceutical compositions can be used in the preparation of individual dosage forms. Consequently, pharmaceutical compositions and dosage forms of the invention comprise the active ingredients disclosed herein. The notation of "active ingredient" signifies the compounds of the invention described herein or salts thereof. Pharmaceutical compositions and dosage forms of the invention can further comprise a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a neoplastic disease or microbial infection may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

As used herein, a "therapeutically effective amount" is an amount sufficient to either inhibit (partially or totally) formation of a tumor or a hematological malignancy or to reduce its further progression or to inhibit the growth of a microbe of interest. For a particular condition or method of treatment, the dosage is determined empirically, using known methods, and will depend upon facts such as the biological activity of the particular compound employed, the means of administrations, the age, health and body weight of the host; the nature and extent of the symptoms, the frequency of treatment; the administration of other therapies and the effect desired. Hereinafter are described various possible dosages and methods of administration with the understanding that the following are intended to be illustrative only. The actual dosages and method of administration or delivery may be determined by one of skill in the art.

Typical illustrative dosage forms of the invention comprise a compound or mixture of compounds of the invention thereof as an active ingredient in an amount of from about 1 mg to about 2000 mg, more preferably from about 25 mg to about 1000 mg, even more preferably from about 50 mg to about 750 mg, and most preferably from about 100 mg to about 500 mg.

For illustrative purposes, dosage levels of the administered active ingredients may be: intravenous, 0.01 to about 20 mg/kg; intramuscular, 0.1 to about 50 mg/kg; orally, 0.05 to about 100 mg/kg; intranasal instillation, 0.5 to about 100 mg/kg; and aerosol, 0.5 to about 100 mg/kg of host body weight.

Expressed in terms of concentration, an active ingredient may be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The active ingredients to be employed as antineoplastic or antimicrobial agents can be easily prepared in such unit dosage form with the employment of pharmaceutical materials which themselves are available in the art and can be prepared by established procedures. The following preparations are illustrative of the preparation of dosage forms of the present invention, and not as a limitation thereof.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an active ingredient, anhydrous lactose, microcrystalline cellulose, polyvinylpyrrolidone, stearic acid, colloidal anhydrous silica, and gelatin.

Delayed Release Dosage Forms Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous, bolus injection, intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts of the active ingredients can be used to further adjust the properties of the resulting composition.

The present invention will now be illustrated by the following non-limiting examples.

EXAMPLES

During an exploration in arctic Alaska for terrestrial and marine microorganisms that might contain anticancer constituents, a tundra specimen on the shore of the Beaufort Sea near Prudhoe Bay was collected and subsequently found to contain a Gram-positive bacterium identified as *Kitasatospora* sp. After this actinomycete was identified by 16S rRNA gene sequence similarity, it was scaled up in a quarter-strength potato dextrose broth over a seven-day fermentation period. A dichloromethane extract of 4 L of broth was concentrated to a residue that inhibited growth of the P388 lymphocytic leukemia and a minipanel of human cancer cell lines. For isolation of the anticancer constituents, the fermentation was scaled up to 380 L, and separation was guided by a bioassay using both the P388 and human cancer cell line systems. The resulting extract (3.4 g) was partitioned between 9:1 $CH_3OH$-water and hexane followed by dilution of the aqueous phase to 3:2 $CH_3OH$-water and extraction with $CH_2Cl_2$. Concentration of the latter phase provided the active fraction (0.50 g, P388 $ED_{50}$ 0.15 µg/mL). Separation of this fraction was guided by the P388 lymphocytic leukemia cell line bioassay and was conducted using a series of gel permeation column separations on Sephadex-20 followed by partition chromatographic separations, again on LH-20, and finally by reversed-phase high-performance liquid chromatographic separations that led to cyclodepsipeptides 1 (10.8 mg), 2 (4.8 mg) and 3 (2.6 mg).

By utilizing a bioassay—(P388 lymphocytic leukemia and a panel of human cancer cell lines) guided separation of a *Kitasatospora* sp. collected from a tundra soil sample taken at the shore of the Beaufort Sea, we have isolated three powerful ($GI_{50}$ to 0.0006 µg/mL) cancer cell growth inhibitors (1-3) and determined their structures. From 380-L fermentations of *Kitasatospora* sp. were obtained 2.6 mg of the new cyclodepsipeptide, kitastatin 1 (3), accompanied by respirantin (1, 10.8 mg) and its valeryl homologue (2, 4.8 mg). The structures were determined by employment of a series of high-resolution mass and 2D-NMR spectroscopic analyses. The stereochemical assignments were based on subsequent total synthesis of depsipeptides 1, as reported in an accompanying contribution.

Results and Discussions

In a high-resolution APCI+ mass spectrum, cyclodepsipeptide 1 showed a molecular ion peak at m/z 748.3657 $[M+1]^+$ that corresponded to molecular formula $C_{37}H_{53}N_3O_{13}$. The comprehensive analyses of $^1H$-, $^{13}C$- and 2D-NMR spectra allowed assignment of the following units: lactyl, 2-hydroxy-3-methylvaleryl, 4-amino-2,2,6-trimethyl-3-oxoheptanoyl, 2-hydroxy-4-methylvaleryl, 2-hydroxy-3-formylaminobenzoyl, and a threonine unit. The connection of the fragments by HMBC-NMR analyses led to assignment of depsipeptide 1 with unknown stereochemistry, as reported for the *Streptomyces* sp. constituent 1 by Urushibata[5] in 1993.

Molecular formula $C_{36}H_{51}N_3O_{13}$ was assigned to cyclodepsipeptide 2 on the basis of APCI+ HRMS results, the molecular ion at m/z 734.3500 $[M+1]^+$ being 14 units ($CH_2$) less than 1. The NMR proton and carbon assignments of cyclodepsipeptide 2 were deduced by comparison with those exhibited in the NMR spectra of 1. Those comparisons revealed a 2-hydroxy-3-methylbutyryl unit in place of the 2-hydroxy-4-methylvaleryl unit of 1 and allowed assignment of cyclodepsipeptide 2, previously described in a 1994 Japanese patent.[12]

The 380-L scale fermentation of *Kitasatospora* sp. was repeated three times in order to obtain sufficient amounts of cyclodepsipeptides 1 and 2 for attempts at obtaining crystals for X-ray crystal structure determinations. Although suitable crystals were not obtained, one of the 380-L fermentations led to isolation of a new cyclodepsipeptide designated kitastatin 1 (3), albeit in very low yield (2.6mg). Kitastatin 1 (3) was obtained as an amorphous powder that gave a high-resolution (APCI+) mass spectral molecular ion at m/z 720.3725 $[M+1]^+$, which corresponds to a formula 28 mass units less than that of cyclodepsipeptide 1. The $^1H$-, $^{13}C$- and HMQC-NMR spectra of kitastatin 1 (Table 1) resembled that of respirantin (1). However, the high-field carbonyl signal corresponding to the aromatic formamide group of 1 was missing. That was further confirmed when $^1H$-, $^1H$-COSY, TOCSY-, and HMBC data were interpreted and pointed to a 3-amino-2-hydroxy-benzoyl segment in place of the aromatic formamide as the only structural difference with cyclodepsipeptide 1. Thus, kitastatin 1 was unequivocally assigned structure 3.[13]

Because suitable crystallization of cyclodepsipeptides 1-3 was not successful and prevented investigation of the stereochemistry by X-ray crystal structure determinations, we initially focused on high-field 2-D NMR approaches to the stereochemistry. In ROESY-NMR experiments, kitastatin 1 (3) showed cross-peaks related to the ring system at H-2/H-3 ($\delta_H$ 5.25/6.02), H-9/H-19 ($\delta_H$ 4.84/1.10) and H-25/NH-9 ($\delta_H$ 2.11/7.53), which suggest a 2S, 3R (or 2R, 3S), 9S and 11S (or 9R and 11R) relationship. Similarly, three-cross peaks at H-2/H-3 ($\delta_H$ 5.24/6.03), H-9/H-19 ($\delta_H$ 4.83/1.09) and H-25/NH-9 ($\delta_H$ 2.09/7.50) were located in the ROESY spectrum of cyclodepsipeptide 1. While these NMR experiments were in progress, we were able to unequivocally assign the stereostructure of 1 and kitastatin 1 (3) as 2S, 3R, 5S, 9S, 11S and 13S by our completion of total syntheses.[13] Since we were unable to make a direct comparison of our cyclodepsipeptides 1 and 2 with authentic samples previously reported,[5,12] there still remains some minor uncertainty.

TABLE 1

$^1$H-and $^{13}$C-NMR Spectral Assignments for
Kitastatin 1 (3, recorded in CD$_2$Cl$_2$, J in Hz)$^a$

| Positions | δ $^{13}$C | δ $^1$H | $^1$H, $^1$H-COSY | HMBC (C to H) |
|---|---|---|---|---|
| 1-CO | 168.0 | | | H-2, H-13 |
| 2-CH | 55.8 | 5.25 (dd, 8.5/2.5) | NH-2, H-3 | H-14 |
| 3-CH | 72.9 | 6.02 (dq, 7.0/2.5) | H-2, H-14 | H-14 |
| 4-CO | 172.3 | | | |
| 5-CH | 72.6 | 4.72 (m) | H-15a, H-15b | |
| 6-CO | 173.7 | | | H-19, H-20 |
| 7-C | 53.7 | | | H-19, H-20 |
| 8-CO | 208.5 | | | H-9, H-19, H-20 |
| 9-CH | 56.0 | 4.84 (dd, 11.0/5.5) | NH-9, H-21 | H-21 |
| 10-CO | 170.4 | | | H-9, H-11 |
| 11-CH | 81.4 | 4.74 (m) | H-25 | H-26 |
| 12-CO | 170.2 | | | H-11, H-13, H-29 |
| 13-CH | 71.6 | 5.80 (q, 6.5) | H-29 | H-29 |
| 14-CH$_3$ | 16.6 | 1.36 (d, 6.5) | H-3 | |
| 15-CH$_2$ | 39.8 | 1.52 (m) | H-5, H-15b | H-16, H-17 |
| | | 1.72 (m) | H-5, H-15a | |
| 16-CH | 24.9 | 1.74 (m) | H-18 | |
| 17-CH$_3$ | 21.6 | 0.89 (d, 6.5) | | H-18 |
| 18-CH$_3$ | 22.9 | 0.94 (d, 7.0) | H-16 | H-17 |
| 19-CH$_3$ | 20.0 | 1.10 (s) | | H-20 |
| 20-CH$_3$ | 24.3 | 1.27 (s) | | H-19 |
| 21-CH$_2$ | 43.3 | 1.80 (2H, t, 8.5) | H-9, H-22 | H-9, H-23, H-24 |
| 22-CH | 25.0 | 1.64 (m) | H-21, H-23, H24 | H-23, H-24 |
| 23-CH$_3$ | 21.1 | 0.92 (d, 7.0) | H-22 | H-21 |
| 24-CH$_3$ | 23.6 | 0.93 (d, 7.0) | H-22 | H-21 |
| 25-CH | 36.9 | 2.11 (m) | H-11, H-26, H27 | H-11, H-27 |
| 26-CH$_3$ | 14.7 | 0.98 (d, 7.0) | H-25 | H-27a |
| 27-CH$_2$ | 25.7 | 1.37 (m) | H-25, H-27b, H-28 | H-27 |
| | | 1.77 (m) | H-27a, H-28 | |
| 28-CH$_3$ | 10.6 | 0.97 (t, 7.5) | H-27a, H-27b | H-27a |
| 29-CH$_3$ | 18.3 | 1.54 (d, 7.0) | H-13 | H-13 |
| 1'-C | 113.3 | | | H-5' |
| 2'-C | 150.9 | | | H-4', H-6' |
| 3'-C | 137.0 | | | H-5' |
| 4'-CH | 118.5 | 6.89 (d, 6.5) | H-5' | H-6' |
| 5'-CH | 119.3 | 6.78 (t, 7.5) | H-4', H-6' | |
| 6'-CH | 114.6 | 7.01 (d, 8.0) | H-5' | H-4' |
| 7'-CO | 171.3 | | | NH-2, H-6' |
| NH-2 | | 7.08 (d, 8.5) | H-2 | |
| NH-9 | | 7.53 (d, 9.5) | H-9 | |
| NH-3' | | 4.00 (s, br) | | |

$^a$500 MHz for $^1$H NMR, 100 MHz for $^{13}$C NMR.

To investigate whether minor variations in the fermentation conditions could lead to a series of new cyclodepsipeptide antineoplastic agents, culture media were modified by adding presumed biochemical precursors, DL-serine, 2-hydroxylvaleric acid, DL-tyrosine, or shikimic acid. Fermentation conditions as well as bioassay guided isolation techniques were otherwise identical. As summarized in Table 2, only cyclodepsipeptides 1 and 2 were otherwise isolated with the addition of the various presumed precursors.

TABLE 2

Results of Fermentation Experiments (Runs A-D)[a]

| CH$_2$Cl$_2$ Fraction and Cyclodepsipeptide Compounds | A (mg) | B (mg) | C (mg) | D (mg) |
|---|---|---|---|---|
| CH$_2$Cl$_2$ Fraction[b] | 60.0 | 92.0 | 185.0 | 140.0 |
| Cyclodepsipeptide 1 | 7.0 | 5.3 | 3.7 | 9.0 |
| Cyclodepsipeptide 2 | 1.7 | 2.0 | 0.9 | 2.3 |

[a]Run A: culture media with addition of DL-serine. Run B: culture media with addition of 2-hydroxyvaleric acid. Run C: culture media with addition of DL-tyrosine. Run D: culture media with addition of shikimic acid.
[b]CH$_2$Cl$_2$ extract fraction (from each 380-L fermentation) obtained from the CH$_2$Cl$_2$/CH$_3$CHOH—H$_2$O (3:2) solvent partition isolation step.

The bioassay-directed separation clearly indicated that cyclodepsipeptides 1-3 are the most important anticancer constituents of *Kitasatospora* sp. When evaluated against the murine P388 lymphocytic leukemia and six human cancer cell lines, they exhibited extraordinary cancer cell growth inhibitory properties (Table 3).

TABLE 3

Inhibition of the Murine P388 Lymphocytic Leukemia (ED$_{50}$ µg/mL) and Human Cancer Cell Lines (GI$_{50}$ µg/mL) by Cyclodepsipeptides 1-3.

| Cyclodepsipeptides | P388 | BXPC-3 | MCF-7 | SF268 | NCI-H460 | KM20L2 | DU-145 |
|---|---|---|---|---|---|---|---|
| 1 | 0.0037 | 0.47 | 0.0006 | 0.0016 | 0.0006 | 0.0006 | 0.00018 |
| 2 | 0.03 | 1.2 | 0.00062 | 0.016 | 0.00063 | 0.00058 | <0.0001 |
| 3 | 0.045 | 0.0066 | 0.004 | 0.0035 | <0.001 | 0.0024 | 0.0026 |

Since the minor structural differences between compounds 1, 2 and 3 did not greatly affect the cancer cell growth inhibitory activities, it appears that the overall stereochemistry of the macrocyclic lactone and side-chain are of greater importance. Structural modifications of kitastatin 1[13] are in progress as well as preclinical development. Interestingly, no previous anticancer activity has been reported for cyclodepsipeptides 1 and 2.[5,12]

In addition to the human cancer cell line activity, cyclodepsipeptide 1 had activity against the pathogenic fungus *Cryptococcus neoformans* (minimum inhibitory concentration [MIC]=2 µg/ml), and cyclodepsipeptide 2 had marginal activity against the opportunistic bacterium *Micrococcus luteus* (MIC=64 µg/ml). Kitastatin 1 (3) had marginal activity against *C. neoformans* and *Enerococcus faecalis* (MIC=64 µg/ml).

General Experimental Procedures.

Solvents used for the chromatographic procedure were redistilled. Sephadex LH-20 employed for gel permeation and partition chromatography was obtained from Pharmacia Fine Chemicals AB, Upsala, Sweden. The silica gel GHLF Uniplates for thin layer chromatography were supplied by Analtech, Inc., USA. The TLC results were viewed under UV light and developed with ceric sulfate/sulfuric acid (heating for 3 minutes). The analytical HPLC was conducted with a Hewlett-Packard model 1100 HPLC coupled with a diode-array detector and an Elastic Light Scattered Detector. Reverse-phase HPLC was performed on a ZORBAX SB C18 column attached to a Waters 600E instrument with a 2487 dual λ absorbance detector.

The melting points were recorded with a Kofler melting point instrument. The optical rotation data were determined with a Perkin-Elmer 241 polarimeter. UV spectra were from a Perkin-Elmer Lambda 3β UV/VIS spectrophotometer equipped with a Hewlett-Packard Laser Jet 2000 plotter. IR spectra were obtained with an AVATAR 360 FT-IR instrument with the sample prepared in CHCl$_3$ film. High-resolution mass spectra were obtained with a JEOL LCmate magnetic sector instrument by APCI+ with a poly(ethylene glycol) reference. The NMR experiments were conducted using a Varian Unity INOVA-500 spectrometer operating at 500 MHz and 400 MHz for $^1$H NMR and 2D NMR and at 100 MHz for $^{13}$C NMR.

Specimen Collection and Fermentation.

Soil samples were collected in clean plastic bags by one of us (GRP) on the shore tundra near Prudhoe Bay (Beaufort Sea), Alaska, and shipped by air to our laboratory. Soils were aseptically diluted and spread on quarter-strength potato dextrose agar (Difco) containing soil extract. *Kitasatospora* sp. was identified by 16S rRNA gene sequence similarity (Accugenix, Newark, Del.). Results from the MicroSeq database based on the first 500 base pairs of the 16S rRNA gene placed the bacterium in the genus *Kitasatospora* sp. (% difference=1.91, confidence level to genus). Isolated colonies were subcultured and fermented in potato dextrose broth/soil extract, and extracts were screened against the murine P388 lymphocytic leukemia cell line and a minipanel of human cancer cell lines. Prior to large-scale fermentation, the P388 and human cancer cell line activity of the actinomycete was determined to be optimum in quarter-strength potato dextrose broth for seven days. All activity peak experiments and large-scale fermentations were performed at room temperature with shaking.

Extraction and Solvent Partition of *Kitasatospora* sp.

The microbial broth (380 L; February 2003-May 2003) was extracted (3×) with CH$_2$Cl$_2$ (½ volume). The CH$_2$Cl$_2$ extract was dried (3.4 g) and then redissolved in 2 L of CH$_2$Cl$_2$—H$_2$O and partitioned (4×) with CH$_2$Cl$_2$ (2 L per pass). The CH$_2$Cl$_2$ was quickly removed in vacuo, and the residue was redissolved in 9:1 CH$_3$OH-water and partitioned (4×) with hexane. After dilution to 3:2 CH$_3$OH—H$_2$O, the aqueous phase was partitioned (4×) with CH$_2$Cl$_2$ to give 0.5 g of a CH$_2$Cl$_2$-soluble fraction (P388 ED$_{50}$, 0.15 µg/mL).

Isolation of Cyclodepsipeptides 1, 2 and 3.

The anticancer CH$_2$Cl$_2$ fraction (0.5 g), obtained as described in the preceding experiment, was passed in CH$_3$OH through a column of Sephadex LH-20. Two resulting bioactive (cancer cell line bioassay) fractions were combined and chromatographed on a Sephadex LH-20 column in hexane-toluene-methanol (3:1:1) as eluent, which led to the concentration into one fraction of the inhibitory activity (57 mg, P388 0.02 µg/mL). Further separation of the active fraction was performed using reverse-phase HPLC. Initially, analytical HPLC of the fraction was conducted on a HP1100 series instrument with both ELSD and UV detectors to locate the target peaks. The fraction was then separated by semi-preparative HPLC on a Waters instrument with a ZORBAX SB C18 column (9.6×250 mm) in acetonitrile-water (40% to 90% in 45 minutes) at 4 mL/minute flow rate. Cyclodepsipeptides 1, 2 and 3 were obtained by concentration of the eluting fractions with peaks at retention times of 42.5, 40 and 45 min, respectively.

The experimental results summarized in Table 2 were obtained by employment of the preceding procedure.

Cyclodepsipeptide 1. Colorless amorphous powder (10.8 mg): mp 118-120° C.; $^1$H NMR (CD$_2$Cl$_2$, 500 MHz) δ 12.61 (1H, s, 2'-OH), 8.54 (1H, d, J=6.0 Hz, H-4'), 8.47 (1H, s, H-8'), 7.92 (1H, s, 3'-NH), 7.50 (1H, d, J=7.5 Hz, 9-NH), 7.40 (1H, d, J=6.0 Hz, H-6'), 7.16 (1H, d, J=7.0 Hz, 2-NH), 6.97 (1H, t, J=6.0 Hz, H-5'), 6.03 (1H, m, H-3), 5.80 (1H, q, J=6.0 Hz, H-13), 5.24 (1H, dd, J=1.6,7.0 Hz, H-2), 4.83 (1H, m, H-9), 4.73 (1H, m, H-11), 4.71 (1H, m, H-5), 2.09 (1H, m, H-25), 1.80 (2H, m, H-21), 1.76 (1H, m, H-27b), 1.70 (1H, m, H-16), 1.68 (1H, m, H-15b), 1.62 (1H, m, H-22), 1.54 (1H, m, H-15a), 1.54 (3H, d, J=6.0 Hz, H-29), 1.36 (3H, d, J=6.0 Hz, H-14), 1.33 (1H, m, H-27a), 1.27 (3H, s, H-20), 1.09 (3H, s, H-19), 0.96 (3H, d, J=6.0 Hz, H-26), 0.95 (3H, t, J=6.0 Hz, H-28), 0.93 (3H, d, J=6.0 Hz, H-18), 0.92 (3H, d, J=6.0 Hz, H-23), 0.91 (3H, d, J=6.0 Hz, H-24), 0.89 (3H, d, J=6.0 Hz, H-17), $^{13}$C NMR (CD$_2$Cl$_2$, 100 MHz) δ 208.0(C-8), 173.7 (C-6), 172.3(C-4), 170.7(C-7'), 170.4(C-10), 170.1(C-12), 167.8(C-1), 159.3(C-8'), 150.9(C-2'), 127.9(C-3'), 125.0(C-4'), 120.7(C-6'), 119.2(C-5'), 113.3(C-1'), 81.4(C-11), 72.7 (C-3), 72.6(C-5), 71.7(C-13), 56.8(C-9), 56.0(C-2), 54.2(C-7), 43.3(C-21), 39.7(C-15), 36.8(C-25), 25.7(C-27), 24.9(C-16), 24.8(C-22), 24.3(C-20), 23.6(C-23), 23.0(C-18), 21.5 (C-17), 21.0(C-24), 20.0(C-19), 18.3(C-29), 16.6(C-14), 14.5(C-26), 10.6(C-28); HRMS (APCI+) m/z 748.3691 [M+H]$^+$ (calcd for C$_{37}$H$_{54}$N$_3$O$_{13}$, 748.3657).

Cyclodepsipeptide 2. Colorless amorphous powder (4.8 mg): mp 117-120° C.; $^1$H NMR (CD$_2$Cl$_2$, 400 MHz) δ 12.62 (1H, s, 4'-OH), 8.53 (1H, d, J=8.0 Hz, H-4'), 8.50 (1H, s, H-8'), 8.02 (1H, s, 3'-NH), 7.52 (1H, d, J=10.0 Hz, 9-NH), 7.43 (1H, d, J=8.0 Hz, H-6'), 7.18 (1H, d, J=8.0 Hz, 2-NH), 6.99 (1H, t, J=7.6 Hz, H-5'), 6.02 (1H, m, H-3), 5.82 (1H, q, J=7.2 Hz, H-13), 5.26 (1H, d, J=8.8 Hz, H-2), 4.85 (1H, m, H-9), 4.77 (1H, m, H-11), 4.54 (1H, m, H-5), 2.12 (1H, m, H-15), 2.10 (1H, m, H-24), 1.83 (2H, t, J=6.0 Hz, H-20), 1.75 (1H, m, H-26b), 1.62 (1H, m, H-21), 1.56 (3H, d, J=6.4 Hz, H-28), 1.39 (3H, d, J=6.4 Hz, H-14), 1.37 (1H, m, H-26a), 1.29 (3H, s, H-19), 1.11 (3H, s, H-18), 0.98 (3H, d, J=6.4 Hz, H-17), 0.98 (3H, d, J=6.4 Hz, H-25), 0.97 (3H, t, J=6.4 Hz, H-27), 0.95 (3H, d, J=6.4 Hz, H-16), 0.92 (3H, d, J=6.4 Hz, H-23), 0.92 (3H, d, J=6.4 Hz, H-24); $^{13}$C NMR (CD$_2$Cl$_2$, 100 MHz) δ. 207.5(C-8), 173.6(C-6), 170.9(C-4), 170.9(C-7'), 170.6(C-10), 170.0(C-12), 167.7(C-1), 159.5(C-8'), 150.8(C-2'), 127.9(C-3'), 125.0(C-4'), 120.7(C-6'), 119.1(C-5), 113.5(C-1'), 81.0(C-11), 78.3(C-5), 72.7(C-3), 71.6(C-13), 56.7(C-9), 55.9(C-2), 53.8(C-7), 42.8(C-20), 36.8(C-24), 30.3 (C-15), 25.4(C-26), 24.8(C-19), 24.1(C-21), 23.6 (C-23), 20.0(C-22), 19.8(C-18), 18.4(C-17), 18.1(C-28), 17.7(C-16), 16.6(C-14), 14.4(C-25), 10.4(C-27); HRMS (APCI+) m/z 734.351 [M+H]$^+$ (calcd for C$_{36}$H$_{52}$N$_3$O$_{13}$, 734.3500).

Cyclodepsipeptide 3. Colorless amorphous powder: mp 126-129° C.; [α]$^{24}_D$ −10 (c 0.07, CH$_3$OH); UV (CH$_3$OH) λ$_{max}$ 231, 328 nm; IR (CHCl$_3$), v. 1745, 1712, 1665, 1644, 1502 and 1525 cm$^{-1}$; HRMS (APCI+) m/z 720.3725[M+H]$^+$ (calcd for C$_{36}$H$_{54}$N$_3$O$_{12}$, 720.3708); $^1$H and $^{13}$C NMR data see Table 1.

Antimicrobial Susceptibility Testing

Cyclodepsipeptides 1 and 2 were screened against the bacteria *Stenotrophomonas maltophilia* ATCC 13637, *Micrococcus luteus* Presque Isle 456, *Staphylococcus aureus* ATCC 29213, *Escherichia coli* ATCC 25922, *Enterobacter cloacae* ATCC 13047, *Enterococcus faecalis* ATCC 29212, *Streptococcus pneumoniae* ATCC 6303, *Neisseria gonorrhoeae* ATCC 49226, and the fungi *Candida albicans* ATCC 90028 and *Cryptococcus neoformans* ATCC 90112, according to established broth microdilution susceptibility assays.[15,16] Owing to a paucity of material, compound 2 was tested against *S. maltophilia*, *M. luteus*, *S. aureus*, *E. coli* and *C. albicans* only. Compounds were reconstituted in a small volume of sterile DMSO and diluted in the appropriate media immediately prior to susceptibility experiments. The minimum inhibitory concentration was defined as the lowest concentration of compound that inhibited all visible growth of the test organism (optically clear). Assays were repeated on separate days.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

References

1. Contribution 560 of the series Antineoplastic Agents. For part 559, see Smith, A. B., III; Razler, T. M.; Pettit, G. R.; Chapuis, J-C. *Organic Lett.* 2005, 7, 4403-4406.
2. Tamamura, T.; Sawa, T.; Isshiki, K.; Masuda, T.; Homma, Y.; Iinuma, H.; Naganawa, H.; Hamada, M.; Takeuchi, T.; Umezawa, H. *J. Antibiot.* 1985, 38(12), 1664-1669.
3. (a) Peczynska-Czoch, W. *Inst. Immunol. Exp. Ther.* 1987, 35(2), 129-137. (b) Peczynska-Czoch, W.; Mordarski, M.; Kaczmarek, L.; Nantka-Namirski, P. *Inst. Immunol. Exp. Ther.* 1987, 35(2), 109-15.
4. Mordarska, H.; Wieczorek, J.; Zakrzewska-Czerwinska, J.; Zwiefka, A.; Mordarski, M. *Inst. Immunol. Exp. Ther.* 1987, 35(2), 237-247.
5. Urushibata, I.; Isogai, A.; Matsumoto, S., Suzuki, A. *J. Antibiot.* 1993, 46(4), 701-703.
6. Caruso, M.; Colombo, A. L.; Crespi-Perellino, N.; Fedeli, L.; Malyszko, J.; Pavesi, A.; Quaroni, S.; Saracchi, M.; Ventrella, G. *Annals of Microbiology* 2000, 50(2); 89-102.
7. Wanigasekera, a.; Hiraga, K.; Hamanaka, N.; Oka, K. *Bioscience, Biotechnology, and Biochemistry* 2001, 65(10), 2353-2357.
8. Momose, I.; Sekizawa, R.; Hirosawa, S.; Ikeda, D.; Naganawa, H.; Linuma, H.; Takeuchi, T. *J. Antibiotics* 2001, 54(12), 1004-1012.
9. Chung, Y. R.; Sung, K. C.; Mo, H. K.; Son, D. .; Nam, J. S.; Chun, J.; Bae, K. S. *International Journal of Systematic Bacteriology* 1999, 49, 753-758.
10. Moon, S-S.; Hwang, W-H.; Chung, Y. R.; Shin, J. *J. Antibiot.*, 2003, 56(10), 856-861.

11. (a) Werner, G.; Hagenmaier, G.; Albert, K.; Kohlshorn, H. Tetrahedron Lett. 1983, 24, 5193-5196. (b) Kretschmer, A.; Dorgerloh, M.; Deeg, M.; Hagenmaier, H. Agric. Biol. Chem. 1985, 49, 2509-2511. (c) Werner, G.; Hagenmaier, G.; Drautz, H.; Baumgartner, A.; Zahner, H. J. Antibiot. 1984, 37, 110-117. (d) Meyer, M.; Keller-Schierlein, W.; Drautz, H.; Blank, W.; Zahner, H. Helv. Chim. Acta 1985, 68, 83-94. (e) Baker, G. H.; Brown, P. J.; Dorgan, R. J.; Everett, J. R.; Ley, S. V.; Slawin, A. M. Z.; Williams, D. J. Tetrahedron Lett. 1987, 28, 5565-5568. (f) O'Shea, M. G.; Richards, R. W.; Rothschild, J. M.; Lacey, E. J. Antibiot. 1997, 50, 1073-1077. (g) Toshima, K.; Yamaguchi, H.; Jyojima, T.; Noguchi, Y.; Nakata, M.; Matsumura, S. Tetrahedron Lett. 1996, 37, 1073-1076. (h) Scheidt, K. A.; Bannister, T. D.; Tasaka, A.; Wendt, M. D.; Savall, B. M.; Fegley, G. J.; Roush, W. R. J. Am. Chem. Soc. 2002, 124, 6981-6990.

12. Suzuki, A.; Nagayama, K. Jpn. Kokai Tokkyo Koho (1994), 15 pp. CODEN: JKXXAF JP 06239844 A2 19940830 Heisei. Application: JP 93-51415 19930217.

13. Pettit, G. R.; Smith, T. H.; Feng, S.; Knight, J. C.; Tan, R.; Pettit, R. K. J. Nat. Prod. 2005, in preparation.

14. NCCLS. Methods for Dilution Antimicrobial Susceptibility Tests for Bacteria That Grow Aerobically; Approved Standard—Fifth Edition. NCCLS document M7-A5 [ISBN 1-56238-394-9]. NCCLS, 940 West Valley Road, Suite 1400, Wayne, Pa. 19087-1898 USA, 2000.

15. NCCLS. Reference Method for Broth Dilution Antifungal Susceptibility Testing o Yeasts; Approved Standard—Second Edition. NCCLS document M27-A2 [ISBN 1-56238-469-4]. NCCLS, 940 West Valley Road, Suite 1400, Wayne, Pa. 19087-1898 USA, 2002.NCCLS. Reference Method for Broth Dilution Antifungal Susceptibility Testing of Yeasts; Approved Standard—Second Edition. NCCLS Document M27-A2; 2002.

What is claimed is:

1. A method of inhibiting cancer cell growth, wherein the cancer cell inhibited is selected from the group consisting of leukemia, pancreas, breast, CNS, lung-NSC, colon, or prostate cancer, in a host inflicted therewith comprising administering to a host a therapeutically effective amount of a compound having the structural formula:

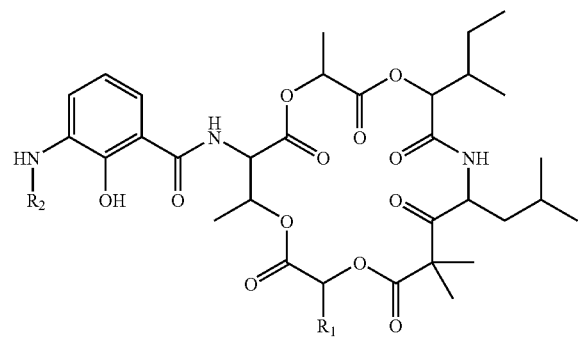

or salts thereof, wherein
$R_1$ is $CH_2CH(CH_3)_2$ or $CH(CH_3)_2$; and
$R_2$ is CHO or H.

2. The method of claim 1, wherein $R_1$ is $CH_2CH(CH_3)_2$.

3. The method of claim 1, wherein $R_2$ is H.

4. The method of claim 2, wherein the compound has the structural formula:

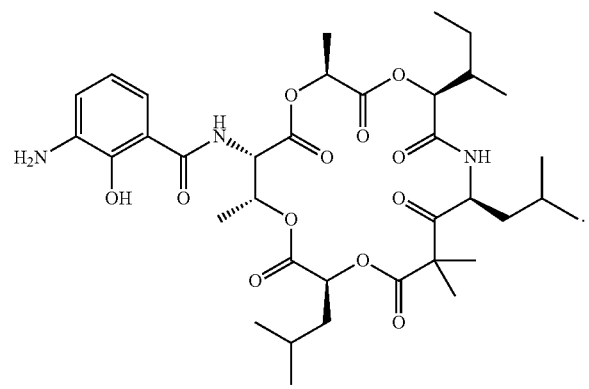 [SMILES: CCC(C)[C@@H]1OC(=O)[C@H](C)OC(=O)[C@@H](NC(=O)c2cccc(N)c2O)[C@@H](C)OC(=O)[C@H](CC(C)C)OC(=O)C(C)(C)C(=O)[C@H](CC(C)C)NC1=O]

5. The method of claim 1, wherein the compound is administered in a pharmaceutical acceptable carrier and is administered in an amount of from about 1 mg to about 2000 mg.

6. The method of claim 5, wherein the compound is administered in an amount of from about 100 mg to about 500 mg.

7. The method of claim 1, wherein the compound is administered intravenous in an amount between 0.01 to about 20 mg/kg; intramuscular in an amount between 0.1 to about 50 mg/kg; orally in an amount 0.05 to about 100 mg/kg; intranasal instillation in an amount between 0.5 to about 100 mg/kg; or aerosol in an amount between 0.5 to about 100 mg/kg of host body weight.

8. A method of inhibiting bacterial growth comprising administering to a host infected with the bacterial growth a therapeutically effective amount of a compound having the structural formula:

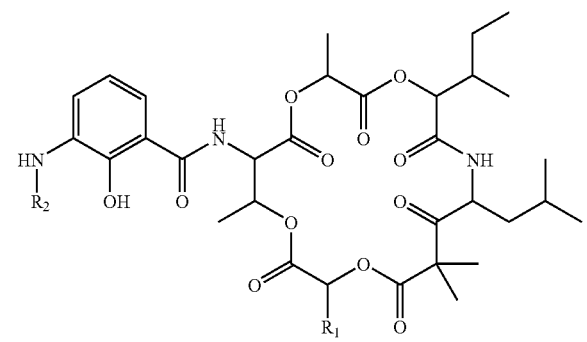

or salt thereof, wherein the compound is in an amount sufficient to inhibit the microbial growth and, wherein
$R_1$ is $CH_2CH(CH_3)_2$ or $CH(CH_3)_2$; and
$R_2$ is CHO or H.

9. The method of claim 8, wherein the $R_1$ is $CH_2CH(CH_3)_2$.

10. The method of claim 8, wherein $R_2$ is H.

11. The method of claim 9, wherein the compound has structural formula:

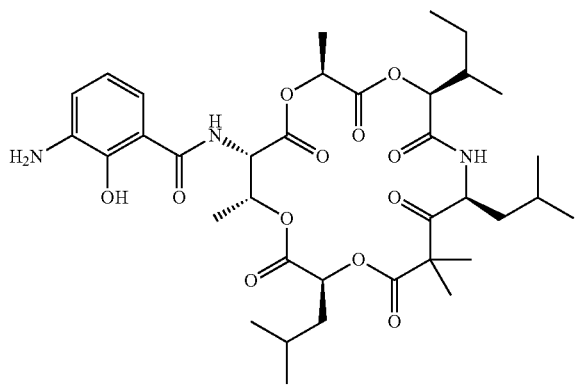

12. The method of claim 8, wherein the compound is in a pharmaceutically acceptable carrier, further comprising administering the compound to a host infected with a microbe in order to contact the microbe with the compound.

13. The method of claim 8, wherein the compound inhibits the growth of at least one of the following: *Enterococcus faecalis, Micrococcus luteus, Stenotrophomonas maltophilia, Staphylococcus aureus, Escherichia coli, Enterobacter cloacae, Streptococcus pneumoniae,* or *Neisseria gonorrhoeae*.

14. A compound in substantially pure form having the structural formula

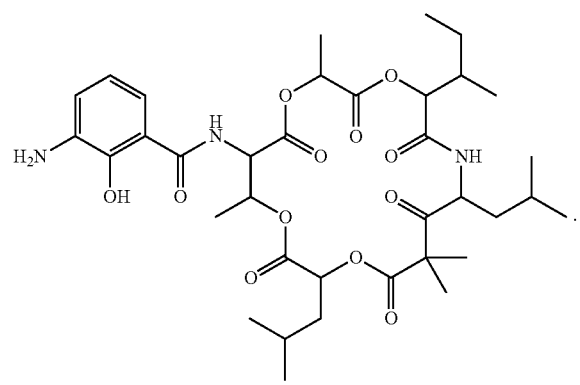 [SMILES: CCC(C)C1OC(=O)C(C)OC(=O)C(NC(=O)c2cccc(N)c2O)C(C)OC(=O)C(CC(C)C)OC(=O)C(C)(C)C(=O)C(CC(C)C)NC1=O]

15. The compound of claim 14, wherein the compound is denominated as Kitastatin 1 having the structural formula:

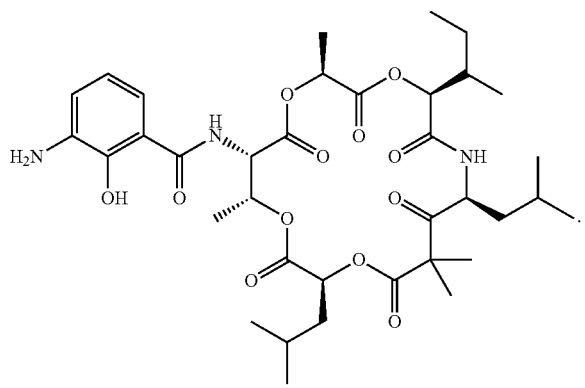 [SMILES: CCC(C)[C@@H]1OC(=O)[C@H](C)OC(=O)[C@@H](NC(=O)c2cccc(N)c2O)[C@@H](C)OC(=O)[C@H](CC(C)C)OC(=O)C(C)(C)C(=O)[C@H](CC(C)C)NC1=O]

16. A composition comprising the compound of claim 14 and a pharmaceutically acceptable carrier.

17. The composition of claim 16, wherein the compound is in a therapeutically effective amount sufficient to inhibit cancer cell growth.

18. The composition of claim 16, wherein the compound inhibits the growth of at least one of the following: *Enterococus faecalis, Micrococcus luteus, Stenotrophomonas maltophilia, Staphylococcus aureus, Escherichia coli, Enterobacter cloacae, Streptococcus pneumoniae,* and *Neisseria gonorrhoeae*.

* * * * *

UNITED STATES PATENT AND TRADEMARK OFFICE
CERTIFICATE OF CORRECTION

| | | |
|---|---|---|
| PATENT NO. | : 8,415,294 B2 | Page 1 of 1 |
| APPLICATION NO. | : 12/598943 | |
| DATED | : April 9, 2013 | |
| INVENTOR(S) | : George R. Pettit et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 340 days.

Signed and Sealed this
Fourth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,415,294 B2　　　　　　　　　　　　　　　　　　　　　Page 1 of 1
APPLICATION NO. : 12/598943
DATED : April 9, 2013
INVENTOR(S) : Pettit et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 583 days.

Signed and Sealed this
First Day of September, 2015

Michelle K. Lee
*Director of the United States Patent and Trademark Office*